United States Patent [19]

Satzinger et al.

[11] 4,415,495
[45] Nov. 15, 1983

[54] 5,6;8,9-TETRAHYDRO-7H-DIBENZ(D,F)AZO-NINES

[75] Inventors: Gerhard Satzinger, Denzlingen; Manfred Herrmann; Edgar Fritschi, both of St. Peter; Heinrich Bahrmann, Kirschzarten; Volker Ganser, Freiburg; Bernd Wagner, Denzlingen; Wolfgang Steinbrecher, Gundelfingen, all of Fed. Rep. of Germany

[73] Assignee: Godecke Aktiengesellschaft, Freiburg, Fed. Rep. of Germany

[21] Appl. No.: 238,501

[22] Filed: Feb. 24, 1981

[30] Foreign Application Priority Data

Jan. 19, 1981 [DE] Fed. Rep. of Germany ....... 3007710

[51] Int. Cl.³ .................. C07D 225/08; A61K 31/355
[52] U.S. Cl. .................... 260/239 D; 424/244
[58] Field of Search .................... 260/239 D; 424/244

[56] References Cited

U.S. PATENT DOCUMENTS 3,751,487  8/1973  Brossi et al. ..................... 568/643
3,932,384  1/1976  Sawa et al. ..................... 260/239 D

FOREIGN PATENT DOCUMENTS 181510 10/1905 Fed. Rep. of Germany.

OTHER PUBLICATIONS

J. Chem. Soc., 947–957, (1952).
J. Amer. Chem. Soc., 80, 445–451, (1958).
J. Amer. Chem. Soc., 89, 2464–2469, (1967).
Kotera, et al., Shionogi Kenyushu Nempo, 17, 88–106 (1967) [Chemical Abstract, 68, 105398t, (1968)].

Primary Examiner—Robert Gerstl
Assistant Examiner—D. Springer
Attorney, Agent, or Firm—Walter Patton

[57] ABSTRACT

The present invention provides 5,6;8,9-tetrahydro-7H-dibenz(d,f)azonine derivatives of the formula:

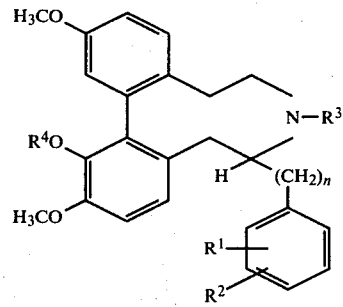

wherein $R^1$ and $R^2$, which are the same or different, are hydrogen or halogen atoms or lower alkyl or alkoxy radicals, $R^3$ is a hydrogen atom or a lower alkyl radical, $R^4$ is a hydrogen atom or a lower alkyl or alkanoyl radical and n is 1 or 2; and the pharmaceutically acceptable salts thereof formed with inorganic and organic acids; but excluding 6-benzyl-2,12-dimethoxy-1-hydroxy-7-methyl-5,6;8,9-tetrahydro-7H-dibenz(d,-f)azonine in which case $R^1$, $R^2$ and $R^4$ are hydrogen, n is 1 and $R^3$ is methyl. The lower alkyl, alkanoyl and alkoxy radicals are straight chained or branched radicals containing 1 to 5 carbon atoms.

The present invention also provides a process for the preparation of these compounds, as well as pharmaceutical compositions containing them.

20 Claims, No Drawings

5,6;8,9-TETRAHYDRO-7H-DIBENZ(D,F)AZONINES

The present invention is directed to novel 5,6;8,9-tetrahydro-7H-dibenz(d,f)azonine derivatives, to their preparation and to compositions containing them.

The present invention provides 5,6;8,9-tetrahydro-7H-dibenz(d,f)azonine derivatives of the general formula:

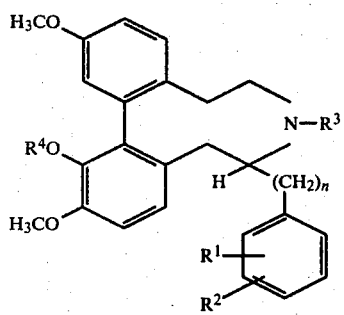

wherein $R^1$ and $R^2$, which are the same or different, are hydrogen or halogen atoms or lower alkyl or alkoxy radicals, $R^3$ is a hydrogen atom or a lower alkyl radical, $R^4$ is a hydrogen atom or a lower alkyl or alkanoyl radical and n is 1 or 2; and the pharmaceutically acceptable salts thereof formed with organic and inorganic acids; but excluding 6-benzyl-2,12-dimethoxy-1-hydroxy-7-methyl-5,6;8,9-tetrahydro-7H-dibenz(d,f)-azonine in which case in formula (I) $R^1$, $R^2$ and $R^4$ are hydrogen, n is 1 and $R^3$ is methyl.

The novel compounds according to the present invention are useful as antiarrhythmic agents and as local anesthetics.

The lower alkyl, alkanoyl and alkoxy radicals in formula (I) are straight chain or branched radicals containing 1 to 5 and preferably 1 to 3 carbon atoms.

Those compounds of formula (I) are preferred in which $R^1$ and $R^2$ are hydrogen, fluorine or chlorine atoms or methyl or methoxy radicals, $R^3$ is a hydrogen atom or a methyl radical and $R^4$ is a hydrogen atom or a methyl or acetyl radical and n is 1 or 2.

However, those compounds of formula (I) in which n is 2 have proved to be especially useful.

It is known that local anesthetics have characteristic side effects. These include, in particular, an undesired vasodilatory effect, which is responsible for the short period of action, and systemic toxicity, which makes necessary a combination with α-sympathomimetic compounds, and a depressive effect on the heart and central nervous system, which gives rise to the danger of bradycardia, with stoppage of the heart and the possibility of respiratory failure. Further, unpleasant side effects include localized tissue irritation and allergic reactions.

Quinidine and procainamide are the prototypes of direct acting antiarrhythmic drugs. However, their use is limited by their property of reducing all base functions of the heart. The necessary high dosage and the small therapeutic index for the therapy of arrhythmia, as well as the markedly unpleasant accompanying phenomena of all known antiarrhythmic drugs, such as the danger of collapse and shock, tachycardia, thrombopoenia, agranulocytosis and gastrointestinal and allergic phenomena, must be taken into account in the case of all previously known antiarrhythmic drugs.

It is an object of the present invention to provide new types of compounds, with especially prolonged action and good compatibility, which are substantially free of the above mentioned side effects.

The process for the preparation of the new compounds of formula (I) is based upon a Grignard reaction with thebaine or northebaine or derivatives thereof. The first attempts to react thebaine with Grignard reagents are described in German Patent Specification No. 181,510. The Grignard reagents used were phenyl and benzyl magnesium bromide. As was found upon repetition of Example 2 of German Patent Specification No. 818,510, under the reaction conditions there chosen, it was not possible to obtain chemically uniform and pure products. The structure of the reaction products was incorrectly stated and there was an absence of all physical properties. The thebaine derivatives according to German Patent Specification No. 181,510, which were based upon a reaction with phenyl Grignard reagents were given the correct dibenzazonine structure in J. Chem. Soc., 1952, p 947.

According to German Patent Specification No. 181,510, the thebaine derivatives obtained at that time were to be used as medicaments, although no indications were given. Although the Grignard reaction of thebaine has also been the subject matter of recent publications (see J.A.C.S., 1958, p 445; 1967, p 2464), which were concerned with the structure of the reaction products, nothing has been reported concerning a potential medicinal effectiveness.

The discovery that the class of compounds of formula (I) contain valuable antiarrhythmic and anesthetic compounds is to be regarded as being extremely surprising since all previously known compounds with the same type of activity have completely different structural features. Thus, for example, mention may be made of local anesthetics, such as tropanes (e.g., eucaine), p-aminobenzoic acid esters (e.g., procaine), N-acylanilines (e.g., lidocaine), dyclonine, pramocaine, phenacaine, mucaine and quinisocaine.

Examples of typical antiarrhythmic agents include quinidine, procainamide, ajmaline, lidocaine, diphenylhydantoin, sparteine, practolol, verapamil and amiodaron. With regard to these active materials, too, there is no structural relationship with formula (I).

The compounds of formula (I) can be prepared, for example, by reacting a compound of the formula:

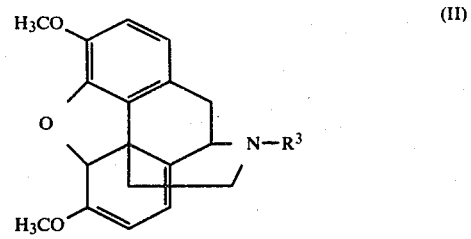

in which $R^3$ has the same meaning as above, with a Grignard reagent of the formula:

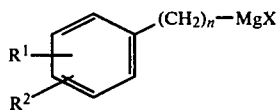

in which $R^1$, $R^2$ and n have the same meanings as above and X is a chlorine, bromine or iodine atom, when $R^4$ is to be a lower alkyl or alkanoyl radical, subsequently O-alkylating or O-acylating and, if desired, subsequently converting the compound obtained of formula (I) into a pharmaceutically acceptable salt by reaction with an organic or inorganic acid.

The preparative process is carried out in the solvents which are conventional for Grignard reactions, for example diethyl ether or an aromatic hydrocarbon, such as benzene or toluene, or in a mixture thereof, at a temperature of from $-15°$ C. to $+20°$ C. Methylene chloride can also be used for this purpose. The decomposition of the Grignard complex can be achieved under especially mild conditions by means of a concentrated aqueous solution of ammonium chloride. The preparation of the Grignard reagents of formula (III) is known and can be catalyzed by elementary iodine.

The starting compounds of formula (II) are also all known and are derived from thebaine or northebaine, insofar as these natural products are not themselves used directly.

The O-alkylation of compounds of formula (I), in which $R^4$ is a hydrogen atom, can be carried out with alkylation agents conventionally used for phenolic groups, for example dialkyl sulphates or diazoalkanes. If $R^4$ is to be a methyl radical, higher yields are obtained when the methylation is carried out in the manner described in Federal Republic of Germany Patent Specification No. 2,757,335 by means of phenyl trimethylammonium hydroxide. The O-acylation can be carried out by known methods using acyl halides or acid anhydrides.

The free bases of formula (I) can be converted into their pharmaceutically acceptable salts by neutralization with an appropriate inorganic or organic acid, for example, hydrochloric acid, sulfuric acid, phosphoric acid, hydrobromic acid, acetic acid, fumaric acid, oxalic acid, lactic acid, citric acid, malic acid, salicylic acid, malonic acid, maleic acid, succinic acid or ascorbic acid.

For the preparation of pharmaceutical compositions, the active materials can be mixed with conventional additives and liquid or solid carrier materials. The compounds of formula (I) can be administered orally or parenterally in liquid or solid form within wide dosage limits.

Conventional additives for liquid forms include, for example, tartarate and citrate buffers, ethanol, complex formers (such as ethylenediaminetetraacetic acid and its non-toxic salts), as well as high molecular weight polymers (such as liquid polyethylene oxide) for viscosity regulation. Examples of solid carrier materials include starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain flavouring and/or sweetening agents.

The individual dosage of the compounds according to the present invention will, depending upon the indication, lie within the range of from 0.1 to 100 mg.

The activity of the new compounds according to the present invention is described in the following experimental reports:

EXPERIMENTAL REPORTS

1. Methods

1.1 Arrhythmias due to extracellular electrolyte disturbance in rats

By means of the intravenous infusion of a calcium chloride solution, arhythmias are induced in narcotised rats which, after termination of the infusion, continue for a certain period of time (modification of the method described by Malinow et al., Arch. Int. Pharmacodyn, 102, 266/1955). This arrhythmic phase is shortened by the prophylactic administration of antiarrhythmic drugs. The activities of the compounds according to the present invention are compared with those of procainamide and phenytoin.

1.2. Electrophysiological investigation of the quinea pig ventricle

The left ventricles of guinea pig hearts are electrically stimulated in an organ bath, the amplitude of contraction being recorded. By means of a second stimulus, the time is determined below which the heart muscle no longer reacts with a separately resolvable contraction. This time is defined as the refractory time.

1.3. Coronary ligature on dogs

Using narcotised dogs, after thoracotomy, a coronary artery (side branch of the R. interventr. post. or of the R. circumflexus) is ligatured (see. A. S. Harris, Circulation, 1, 1318/1950). The heart rhythm disturbances which occur as a result thereof are, on the day following the operation, recorded on the awake animals and treated with the compounds according to the present invention by intragastral and intravenous administration. Procainamide is used as a positive standard. From the ECG, the time is determined in which, after administration of the test compound, a sinus rhythm can be recognized.

1.4. Local anesthetic action on the rabbit eye

The corneal reflex is induced in rabbits using a horse hair which bends with a pressure of about 250 mg (modification of the method described by M. von Frey, Beitrage zur Physiologie des Schmerzsinns, Vehr. d. Kgl. Sachs, Ges. d. Wiss. zu Leipzig, Math.-phys. Kl., 46, 185/1894; Untersuchungen uber die Sinnesfunktionen der menschlichen Haut, Leipzig, 1896). After instillation of local anesthetics into the conjunctival sac of the eye, the number of impacts with the horse hair which result in closure of the eyelid is increased. At intervals of 4 minutes, in each case a maximum of 100 successive impacts are carried out and such an action is taken as being 100%. The period of investigation is at most 60 minutes. The action of the compounds according to the present invention is compared with that of tetracaine and procainamide.

1.5. Acute toxicity in mice

The compounds according to the present invention are administered intragastrally to male mice (NMRI) with a body weight of from 20 to 25 g. Each dosage group consists of 4 animals. The $LD_{50}$ values are determined after having observed the animals for 7 days.

2. Results

2.1. Arrhythmias on rats

The results of the experiments with calcium chloride induced arrhythmias on rats are summarized in the following Table I. The average period of arrhythmia is calculated from experiments with at least 10 animals.

All the compounds according to the present invention shortened the period of arrhythmia in comparison with the control animals to which no compounds with antiarrhythmic action have been administered.

The action of the compounds according to the present invention is better than that of procainamide or, in the case of the compound of Example 11, just as good with regard to the period of arrhythmia. In this experimental model, phenytoin did not exhibit an antiarrhythmic action.

The experiments demonstrated the very favorable therapeutic spectrum of the compounds according to the present invention.

TABLE III

Action of the compound of Example 1 on dogs with coronary ligature

| | Compound of Example 1 | | | | |
|---|---|---|---|---|---|
| dosage mg/kg | 4 i.v. | 10 i.g. | 15 i.g. | 20 i.g. | 25 i.g. |
| average period of eurhythmia (min.) | 62 | 49 | 99 | 105 | 198 |

TABLE IV

Action of the compound of Example 4 on dogs with coronary ligature

| | Compound of Example 4 | | | |
|---|---|---|---|---|
| dosage mg/kg | 4 i.v. | 40 i.g. | 60 i.g. | 80 i.g. |
| average period of eurhythmia (min.) | 68 | 91 | 103 | 139 |

TABLE I

| | | | | Rats with calcium chloride induced arrhythmias | | | | | | | | | | |
|---|---|---|---|---|---|---|---|---|---|---|---|---|---|---|
| Test Compound | Control | Procainamide | Phenyltoin | Compound of Example No. | | | | | | | | | | |
| | | | | 1 | 2 | 3 | 4 | 5 | 6 | 7 | 8 | 9 | 10 | 11 | 12 |
| mg/kg I.V. | — | 10 | 20 | 2.5 | 10 | 10 | 5 | 10 | 5 | 4 | 4 | 4 | 5 | 2.5 | 8 | 5 |
| average period of arrhythmia (min.) | 10.9 | 7.3 | 16.5 | 4.0 | 4.9 | 5.4 | 4.6 | 2.3 | 4.1 | 4.6 | 4.1 | 5.7 | 6.8 | 5.4 | 7.7 | 6.4 |

2.2. Refractory time of the guinea pig left ventricle

The refractory times of the guinea pig ventricles determined by the described method were between 161 and 200 ms. The following Table II contains information concerning the maximum tested compound concentrations, as well as the average prolongation of the refractory time measured at this concentration in comparison with the initial value of, in each case, at least 6 experiments.

The new compounds according to the present invention have an activity which is better than that of the comparison compounds ajmaline, phenytoin, procainamide and verapamil.

TABLE V

Action of the compound of Example 10 on dogs with coronary ligature

| | Compound of Example 10 | | | |
|---|---|---|---|---|
| dosage mg/kg | 2 i.v. | 5 i.g. | 10 i.g. | 40 i.g. |
| average period of eurhythmia (min.) | 40 | 105 | 169 | 185 |

TABLE II

| | | | | | Refractory time of electrically stimulated guinea pig left ventricles | | | | | | | | | | |
|---|---|---|---|---|---|---|---|---|---|---|---|---|---|---|---|
| Test Compound | Ajmaline | Phenyltoin | Procainamide | Verapamil | Compound of Example No. | | | | | | | | | | |
| | | | | | 1 | 2 | 3 | 4 | 5 | 7 | 8 | 9 | 10 | 11 | 12 |
| test compound in the bath (g/ml) | $10^{-5}$ | $10^{-5}$ | $10^{-5}$ | $10^{-5}$ | $10^{-6}$ | $10^{-6}$ | $10^{-5}$ | $10^{-5}$ | $10^{-6}$ | $10^{-6}$ | $10^{-6}$ | $10^{-5}$ | $10^{-6}$ | $10^{-5}$ | $10^{-5}$ |
| prolongation of the refractory time (ms) | 16 | −6 | 7 | 16 | 43 | 46 | 29 | 21 | 25 | 18 | 21 | 27 | 44 | 29 | 51 |

2.3. Dogs with coronary ligature

The compounds of Examples 1 (Table III), 4 (Table IV) and 10 (Table V) were tested on dogs with a coronary ligature. The results with procainamide are given in Table VI. All the compounds were, in each case, tested on at least 5 animals.

The tested compounds according to the present invention act intravenously, even in small doses, better than procainamide. Their enteral effectiveness after intragastral administration could not be demonstrated.

TABLE VI

Action of procainamide on dogs with coronary ligature

| dosage mg/kg | procainamide 10 i.v. |
|---|---|
| average period of eurhythmia (min.) | 19 |

2.4. Local anesthetic action

The following Table VII contains the results of the experiments on the rabbit eye. There are also given, in addition to the concentrations of the test solutions which were instilled into the conjunctival sac, the actions of the compounds in % (see description of the method), as well as their period of action. In each case, the observations were discontinued after 60 minutes.

In this experimental model, procainamide is inactive, whereas tetracaine manifests its maximum activity strength (100%) for 44 minutes. The compounds according to the present invention display a longer period of activity.

TABLE VII

Local anaesthetic action on the rabbit eye

| Compound of Example No. | Concentration in % | Action in % | Period of Action in Min. |
|---|---|---|---|
| 1 | 0.1 | 89 | about 49 |
|   | 0.5 | 100 | >60 |
| 2 | 0.1 | 78 | 46 |
|   | 0.5 | 100 | about 52 |
|   | 1.0 | 100 | >60 |
| 3 | 0.5 | 100 | >60 |
| 5 | 1.0 | 100 | >60 |
| 6 | 1.0 | 79 | >60 |
|   | 2.0 | 100 | >60 |
| 7 | 0.5 | 63 | >60 |
|   | 1.0 | 100 | >60 |
| 8 | 0.5 | 74 | >60 |
|   | 2.0 | 100 | >60 |
| 10 | 1.0 | 100 | >60 |
| 11 | 1.0 | 55 | >60 |
|   | 2.0 | 100 | >60 |
| 12 | 0.1 | 68 | about 56 |
|   | 0.25 | 100 | >60 |
| procainamide | 0.5 | 1 | 0 |
|   | 2.0 | 1 | 0 |
| tetracaine | 0.1 | 100 | about 44 |

TABLE VIII

Acute toxicity in mice

| Compound of Example No. | LD$_{50}$ mg/kg (i.g.) |
|---|---|
| 1 | 680 |
| 2 | 1000 |
| 3 | 600 |
| 4 | 1200 |
| 5 | about 1000 |
| 6 | about 300 |
| 7 | 900 |
| 8 | 1200 |
| 10 | 600 |
| 11 | >1600 |
| 12 | 1200 |
| procainamide | 1200 |
| phenyltoin | 150 |

The following Examples are given for the purpose of illustrating the present invention:

EXAMPLE 1

(−)-6-Benzyl-2,12-dimethoxy-1-hydroxy-7-methyl-5,6;8,9-tetrahydro-7H-dibenz(d,f)azonine A solution of a Grignard reagent is prepared from 5.4 g magnesium turnings and 25 ml benzyl chloride (0.23 mol in each case) in 125 ml anhydrous diethyl ether. A solution of 31.1 g (0.1 mol) thebaine in 450 ml anhydrous benzene is added dropwise thereto in the course of 25 minutes. The resulting yellow solution is subsequently headed under reflux for 2 hours, then cooled, decomposed with a concentrated aqueous solution of ammonium chloride and filtered over silica gel. The organic phase is separated off, first extracted with water and then with 1 N hydrochloric acid. The hydrochloric acid phase is neutralized with a 2 N aqueous solution of sodium carbonate and the precipitated product taken up in ethyl acetate. By the careful addition of a saturated solution of hydrogen chloride in ethyl acetate, an oily by-product is first precipitated out. From the decanted off solution, the hydrochloride of the desired product is then precipitated out by the addition of further ethyl acetate/hydrogen chloride. There are obtained 9.9 g (23% of theory) (−)-6-benzyl-2,12-dimethoxy-1-hydroxy-7-methyl-5,6;8,9-tetrahydro-7H-dibenz(d,-f)azonine hydrochloride. After recrystallization from propan-2-ol there are obtained colorless crystals with a melting point of 245°-246° C.; $[\alpha]_D^{20} = -28.70°$ (c,1 water).

EXAMPLE 2

(−)-6-(3'-Methoxybenzyl)-2,12-dimethoxy-1-hydroxy-7-methyl-5,6;8,9-tetrahydro-7H-dibenz(d,f)azonine A solution of a Grignard reagent is prepared from 5.4 g (0.225 mol) iodine activated magnesium turnings and 34.5 g (0.225 mol) freshly prepared m-methoxybenzyl chloride in 200 ml dry diethyl ether. This Grignard reagent is reacted with 31.1 g (0.1 mol) thebaine and worked up in the manner described in Example 1. There are obtained 14.3 g (30.5% of theory) (−)-6-(3'-methoxybenzyl)-2,12-dimethoxy-1-hydroxy-7-methyl-5,6;-8,9-tetrahydro-7H-dibenz(d,f)azonine hydrochloride. After recrystallization from ethanol, the product is obtained in the form of colorless crystals; mp 248.5° C.; $[\alpha]_D^{20} = -45.9°$ (c,1 water).

EXAMPLE 3

(−)-6-(4'-Fluorobenzyl)-2,12-dimethoxy-1-hydroxy-7-methyl-5,6;8,9-tetrahydro-7H-dibenz(d,f)azonine A solution of a Grignard reagent is prepared from 8.2 g (0.34 mol) magnesium turnings (activated with iodine) and 63.2 g (0.34 mol) p-fluorobenzyl bromide in 350 ml anhydrous diethyl ether. The Grignard reagent is reacted with 36.5 g (0.15 mol) thebaine, dissolved in 600 ml benzene, and worked up in the manner described in Example 1. There are obtained 17.6 g (25% of theory) (−)-6-(4'-fluorobenzyl)-2,12-dimethoxy-1-hydroxy-7-methyl-5,6;8,9-tetrahydro-7H-dibenz(d,f)-azonine hydrochloride containing 0.5 mole water of crystallization. After recrystallization from propan-2-ol, the product is obtained in the form of colorless crystals; mp 222° C.; $[\alpha]_D^{20} = -31.7°$ (c,1 water).

EXAMPLE 4

(−)-6-(2'-Chlorobenzyl)-2,12-dimethoxy-hydroxy-7-methyl-5,6;8,9-tetrahydro-7H-dibenz(d,f)azonine A solution of a Grignard reagent is prepared from 4.4 g (0.18 mol) iodine activated magnesium turnings and 28.4 g (0.18 mol) o-chlorobenzyl chloride in 100 ml anhydrous diethyl ether. The Grignard reagent is reacted with 12.5 g (0.04 mol) thebaine in 225 ml anhydrous benzene and worked up as described in Example 1. There are obtained 14.5 g (76.5% of theory) (−)-6-(2'-chlorobenzyl-2,12-dimethoxy-1-hydroxy-7-methyl-5,6;-8,9-tetrahydro-7H-dibenz(d,f)azonine hydrochloride in the form of colorless crystals which, after recrystallization from ethyl acetate/propan-2-ol (1:1 v/v), melt at 240° C.; $[\alpha]_D^{20} = -138.4°$ (c,1 water).

EXAMPLE 5

(±)-6-Benzyl-7-methyl-5,6;8,9-tetrahydro-1,2,12-trimethoxy-7H-dibenz(d,f)azonine The base is liberated from 13.2 g (0.03 mol) (−)-6-benzyl-2,12-dimethoxy-1-hydroxy-7-methyl-5,6;-8,9-tetrahydro-7H-dibenz(d,f)azonine hydrochloride (prepared by the process of Example 1) by means of a 2 N aqueous solution of sodium carbonate and this free base taken up in a mixture of 50 ml toluene and 5 ml dimethylformamide. The solution is heated to 100°–105° C. and then mixed with 0.09 mol of a 20% solution of phenyltrimethylammonium hydroxide in methanol. The reaction mixture is heated for 1.5 hours in such a manner that methanol distills off simultaneously, the boiling point of the reaction mixture finally being about 140° C. The reaction mixture is then further heated at this temperature for 1 hour, whereafter the solvent is removed in a vacuum and the residue freed from dimethylaniline by steam distillation. The residue is chromatographed on 125 g silica gel (0.003–0.2 mm) in toluene. Elution is carried out by means of about 0.6 liter toluene containing 1% ethanol, and the fractions tested spectroscopically by IR/NMR. Pure product (GC purity 98.5%) is obtained as a non-crystalline, almost colorless resin (TLC: silica gel F 254, methanol/HCL 1:9 v/v, $R_F$ 0.55). There are obtained 7.8 g (65% of theory) (±)-6-benzyl-7-methyl-5,6;8,9-tetrahydro-1,2,12-trimethoxy-7H-dibenz(d,f)azonine.

EXAMPLE 6

(−)-6-(3′-Methoxybenzyl)-7-methyl-5,6;8,9-tetrahydro-1,2,12-trimethoxy-7H-dibenz(d,f)azonine 8.5 g (0.02 mol) (−)-6-(3′-Methoxybenzyl)-2,12-dimethoxy-1-hydroxy-7-methyl-5,6;8,9-tetrahydro-7H-dibenz(d,f)azonine (obtained by the process of Example 2), dissolved in 50 ml toluene and 5 ml dimethylformamide, are mixed with 0.08 mol of a 20% solution of phenyltrimethylammonium hydroxide in methanol and reacted in a manner analogous to that described in Example 5 and then worked up. The product is purified by column chromatography on 80 g silica gel (0.063–0.2 mm). There are obtained 6.2 g (69.4% yield) (−)-6-(3′-methoxybenzyl)-7-methyl-5,7;8,9-tetrahydro-1,2,12-trimethoxy-7H-dibenz(d,f)azonine in the form of an almost colorless resin. TLC (silica gel F 254, methanol/chloroform 1:9 v/v, $R_F$=0.55) GC purity 99.3%; $[\alpha]_D^{20}$= −3.7° (c,1 methanol).

EXAMPLE 7

(−)-1-Acetoxy-6-(3′-methoxybenzyl)-7-methyl-5,6;8,9-tetrahydro-2,12-dimethoxy-7H-dibenz(d,f)azonine 15.2 g (0.032 mol) (−)-6-(3′-Methoxybenzyl)-2,12-dimethoxy-1-hydroxy-7-methyl-5,6;8,9-tetrahydro-7H-dibenz(d,f)azonine (obtained by the process of Example 2) are heated for 6 hours at 120° to 130° C. with 50 ml acetic anhydride. The bulk of the acetic anhydride is then distilled off in a vacuum. The residue is partitioned between water and diethyl ether and the ethereal phase is extracted with an aqueous solution of sodium carbonate. The residue remaining after evaporation of the organic phase in vacuo is taken up in toluene and chromatographed on 250 g silica gel (0.06–0.2 mm), using, as elution agent, toluene+1% methanol. There are obtained 10.0 g (65.7% of theory) (−)-1-acetoxy-6-(3′-methoxybenzyl)-7-methyl-5,6;8,9-tetrahydro-2,12-dimethoxy-7H-dibenz-(d,f)azonine in the form of an almost colorless resin. TLC: silica gel F 254, methanol/chloroform 1:9 v/v; $R_F$=0.55; GC purity 99.7%; $[\alpha]_D^{20}$= −9.0° (c,1 methanol).

EXAMPLE 8

(−)-1-Acetoxy-6-benzyl-2,12-dimethoxy-7-methyl-5,6;8,9-tetrahydro-7H-dibenz(d,f)azonine 9.0 g (0.02 mol) (−)-6-Benzyl-2,12-dimethoxy-1-hydroxy-7-methyl-5,6;8,9-tetrahydro-7H-dibenz(d,f)azonine (obtained by the process of Example 1) are reacted and worked up in a manner analogous to that described in Example 3. There are obtained 8.7 g (97% of theory) (−)-1-acetoxy-6-benzyl-2,12-dimethoxy-7-methyl-5,6;8,9-tetrahydro-7H-dibenz(d,f)azonine in the form of an almost colorless resin. TLC: silica gel F 254, methanol/chloroform 1:9 v/v, $R_F$=0.5, GC purity 95.3%: $[\alpha]HD\ D^{20}$= −2.5° (c,1 methanol).

EXAMPLE 9

6-Benzyl-2,12-dimethoxy-1-hydroxy-5,6;8,9-tetrahydro-7H-dibenz(d,f)azonine

A solution of a Grignard reagent is prepared from 8.5 g (0.35 mol) magnesium turnings and 40 ml (0.35 mol) benzyl chloride in anhydrous diethyl ether. This is reacted with 30 g (0.1 mol) northebaine at 30° C. in tetrahydrofuran. After 2 hours at 55° C., the reaction mixture is mixed with a saturated aqueous solution of ammonium chloride and subsequently worked up. There are obtained 15 g of crude base which is purified by column chromatography (silica gel/toluene+2% methanol). 6-Benzyl-2,12-dimethoxy-1-hydroxy-5,6;8,9-tetrahydro-7H-dibenz(d,f)azonine is obtained in the form of colorless crystals which can be recrystallized from ethyl acetate/methylene chloride; mp 62°–65° C.

EXAMPLE 10

(+)-2,12-Dimethoxy-1-hydroxy-7-methyl-6-phenethyl-5,6;8,9-tetrahydro-7H-dibenz(d,f)azonine A solution of a Grignard reagent is prepared from 5.5 g (0.23 mol) activated magnesium turnings and 41.5 g (0.24 mol) phenethyl bromide in 200 ml anhydrous diethyl ether. To this is added dropwise, at 35°–40° C., a solution of 31.5 g (0.1 mol) thebaine in 0.4 liters dry benzene. After heating under reflux for 2 hours, the reaction mixture is decomposed with a solution of 48 g ammonium chloride in 200 ml water. The usual working up, after conversion of the base into the hydrochloride by means of hydrogen chloride in ethyl acetate, gives 7.3 g (21% of theory) (+)-2,12-dimethoxy-1-hydroxy-7-methyl-6-phenethyl-5,6;8,9-tetrahydro-7H-dibenz(d,-f)azonine hydrochloride; mp 227.6° C., after recrystallization from propan-2-ol.

EXAMPLE 11

(−)-6-(2′,6′-Dichlorobenzyl)-2,12-dimethoxy-7-methyl-1-hydroxy-5,6;8,9-tetrahydro-7H-dibenz(d,f)azonine A solution of a Grignard reagent is prepared from 6.6 g (0.265 mol) activated magnesium turnings and 54.3 g (0.265 mol) 2,6-dichlorobenzyl chloride in dry diethyl ether. The reaction with 39 g (0.125 mol) thebaine takes place in the above described manner in dry benzene. The reaction mixture is stirred for 2 hours at 60° C. and then decomposed with a concentrated aqueous solution of ammonium chloride. After separating off the organic material and working up, there is obtained the crude base which is converted into the hydrochloride by means of hydrogen chloride in ethyl acetate. There are obtained 34.5 g (52% of theory) (−)-6-(2',6'-dichlorobenzyl)-2,12-dimethoxy-7-methyl-1-hydroxy-5,6;8,9-tetrahydro-7H-dibenz(d,f)azonine hydrochloride; mp 255° C., after recrystallization from propan-2-ol.

EXAMPLE 12

(−)-6-(3'-Methylbenzyl)-2,12-dimethoxy-7-methyl-1-hydroxy-5,6;8,9-tetrahydro-7H-dibenz(d,f)azonine A solution of a Grignard reagent is prepared from 7.7 g (0.31 mol) magnesium turnings and 57 g (0.31 mol) 3-methylbenzyl bromide in dry diethyl ether in a manner analogous to that described in Example 1. It is then mixed with a solution of 45.5 g (0.145 mol) thebaine in 525 ml benzene. The reaction is completed by heating to 50° C. for 2 hours. Working up in the usual way gives 40 g of crude base from which, by means of hydrogen chloride in ethyl acetate/propan-2-ol (2:1 v/v), there is precipitated (−)-6-(3'-methylbenzyl)-2,12-dimethoxy-7-methyl-1-hydroxy-5,6;8,9-tetrahydro-7H-dibenz(d,f)azonine hydrochloride. The yield is 15.1 g (31% of theory); mp 256° C., after crystallization from propan-2-ol.

We claim:

1. 5,6;8,9-Tetrahydro-7H-dibenz(d,f)-azonine compounds of the formula:

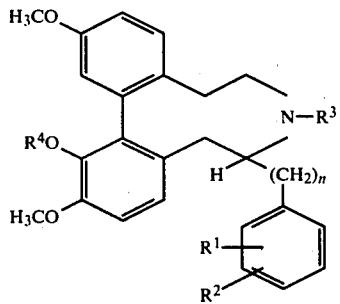

wherein $R^1$ and $R^2$, which are the same or different, are hydrogen, halogen or lower alkyl or alkoxy wherein lower alkyl and alkoxy are straight chained or branched having 1 to 3 carbon atoms $R^3$ is a hydrogen atom or a lower alkyl; $R^4$ is a hydrogen atom or a lower alkyl or alkanoyl and n is 1 or 2; wherein lower alkyl, alkanoyl and alkoxy are straight chained or branched having 1 to 5 carbon atoms; and the pharmaceutically acceptable salts thereof with the proviso that $R^1$, $R^2$, $R^4$ are not all hydrogen when n is 1 and $R^3$ is methyl.

2. Compounds according to claim 1, wherein $R^1$ and $R^2$, which are the same or different, are hydrogen, fluorine or chlorine atoms or methyl or methoxy, $R^3$ is a hydrogen atom or methyl, $R^4$ is a hydrogen atom or methyl or acetyl.

3. Compounds according to claim 1 or 2, wherein n is 2.

4. (−)-6-(3'-Methoxybenzyl)-2,12-dimethoxy-1-hydroxy-7-methyl-5,6;8,9-tetrahydro-7H-dibenz(d,f)azonine.

5. (−)-6-(4'-Fluorobenzyl)-2,12-dimethoxy-1-hydroxy-7-methyl-5,6;8,9-tetrahydro-7H-dibenz(d,f)azonine.

6. (−)-6-(2'-Chlorobenzyl)-2,12-dimethoxy-1-hydroxy-7-methyl-5,6;8,9-tetrahydro-7H-dibenz(d,f)azonine.

7. (+)-6-Benzyl-7-methyl-5,6;8,9-tetrahydro-1,2,12-trimethoxy-7H-dibenz(d,f)azonine.

8. (−)-6-(3'-Methoxybenzyl)-7-methyl-5,6;8,9-tetrahydro-1,2,12-trimethoxy-7H-dibenz(d,f)azonine.

9. (−)-1-Acetoxy-6-(3'-methoxybenzyl)-7-methyl-5,6;8,9-tetrahydro-2,12-dimethoxy-7H-dibenz(d,f)azonine.

10. (−)-1-Acetoxy-6-benzyl-2,12-dimethoxy-7-methyl-5,6;8,9-tetrahydro-7H-dibenz(d,f)azonine.

11. 6-Benzyl-2,12-dimethoxy-1-hydroxy-5,6;8,9-tetrahydro-7H-dibenz(d,f)azonine.

12. (+)-2,12-Dimethoxy-1-hydroxy-7-methyl-6-phenethyl-5,6;8,9-tetrahydro-7H-dibenz(d,f)azonine.

13. (−)-6-(2',6'-Dichlorobenzyl)-2,12-dimethoxy-7-methyl-1-hydroxy-5,6;8,9-tetrahydro-7H-dibenz(d,f)azonine.

14. (−)-6-(3'-Methylbenzyl)-2,12-dimethoxy-7-methyl-1-hydroxy-5,6;8,9-tetrahydro-7H-dibenz(d,f)-azonine.

15. The compounds of claim 1 wherein said lower alkyl, alkanoyl, and alkoxy have 1-3 carbon atoms.

16. The compounds of claim 15 wherein n is 2.

17. The compounds of claim 1 or 19 wherein said lower alkyl, alkanoyl, and alkoxy are straight chained.

18. The compounds of claim 17 wherein n is 2.

19. The compounds of claim 1 wherein $R^1$ and $R^2$, which are the same or different are methyl or methoxy.

20. The compounds of claim 19 wherein n is 2.

* * * * *